United States Patent [19]

Matthews

[11] 4,306,570

[45] Dec. 22, 1981

[54] COUNTER ROTATING BIOPSY NEEDLE

[76] Inventor: Larry S. Matthews, 1609 S. University, Ann Arbor, Mich. 48104

[21] Appl. No.: 179,753

[22] Filed: Aug. 20, 1980

[51] Int. Cl.³ ............................................. A61B 10/00
[52] U.S. Cl. .................................. 128/754; 128/755; 128/310; 408/206
[58] Field of Search ............... 128/754, 755, 753, 310; 408/204, 206

[56] References Cited

U.S. PATENT DOCUMENTS

| | | | |
|---|---|---|---|
| 2,919,692 | 1/1960 | Ackermann | 128/754 |
| 3,587,560 | 6/1971 | Glassman | 408/204 NR |
| 3,778,179 | 12/1973 | Rivas | 408/206 |
| 4,142,517 | 3/1979 | Stavropoulos | 128/754 |
| 4,177,797 | 12/1979 | Baylis et al. | 128/754 |
| 4,230,123 | 10/1980 | Hawkins, Jr. | 128/658 |

*Primary Examiner*—Kyle L. Howell
*Attorney, Agent, or Firm*—Sherman & Shalloway

[57] ABSTRACT

An universally applicable biopsy needle includes two counter-rotating tubes having oppositely facing sawteeth formed on the distal ends thereof. A gear system transmits a driving force to the tubes, causing the counter-rotation which permits the sawteeth to act in a sawing manner for penetration of bone samples and in a cutting manner for soft tissues. Use of an outer cannula allows safe insertion of the needle to the location of the desired sample, and various grasping means are used to extract the sample core. The concentric, telescoping needles provide a sample preserving the natural architecture and orientation of the tissue or cell types, while minimizing harming and maceration of the same.

23 Claims, 6 Drawing Figures

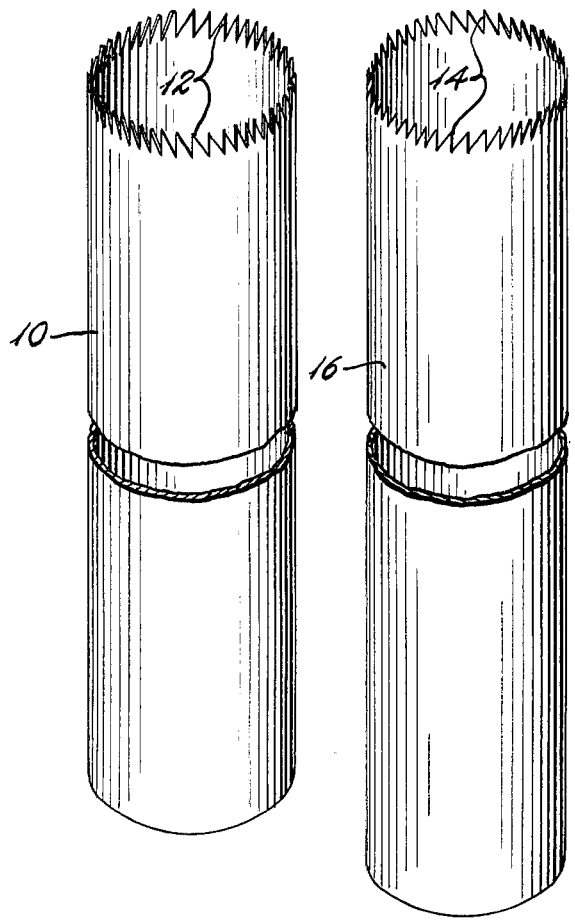
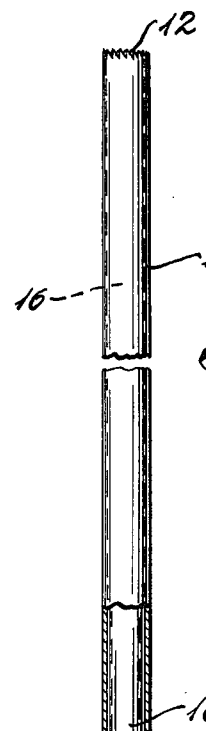
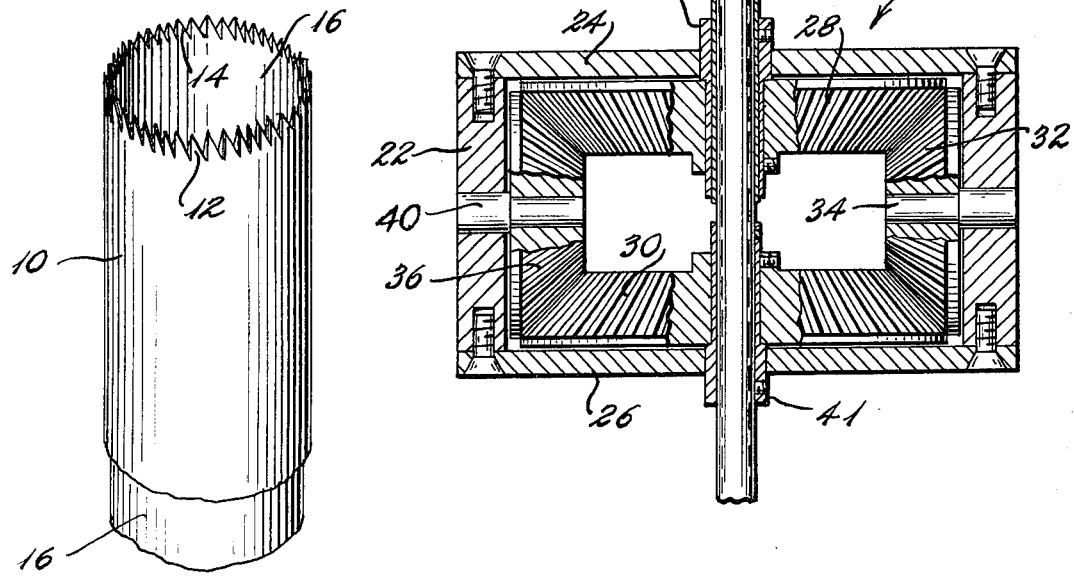

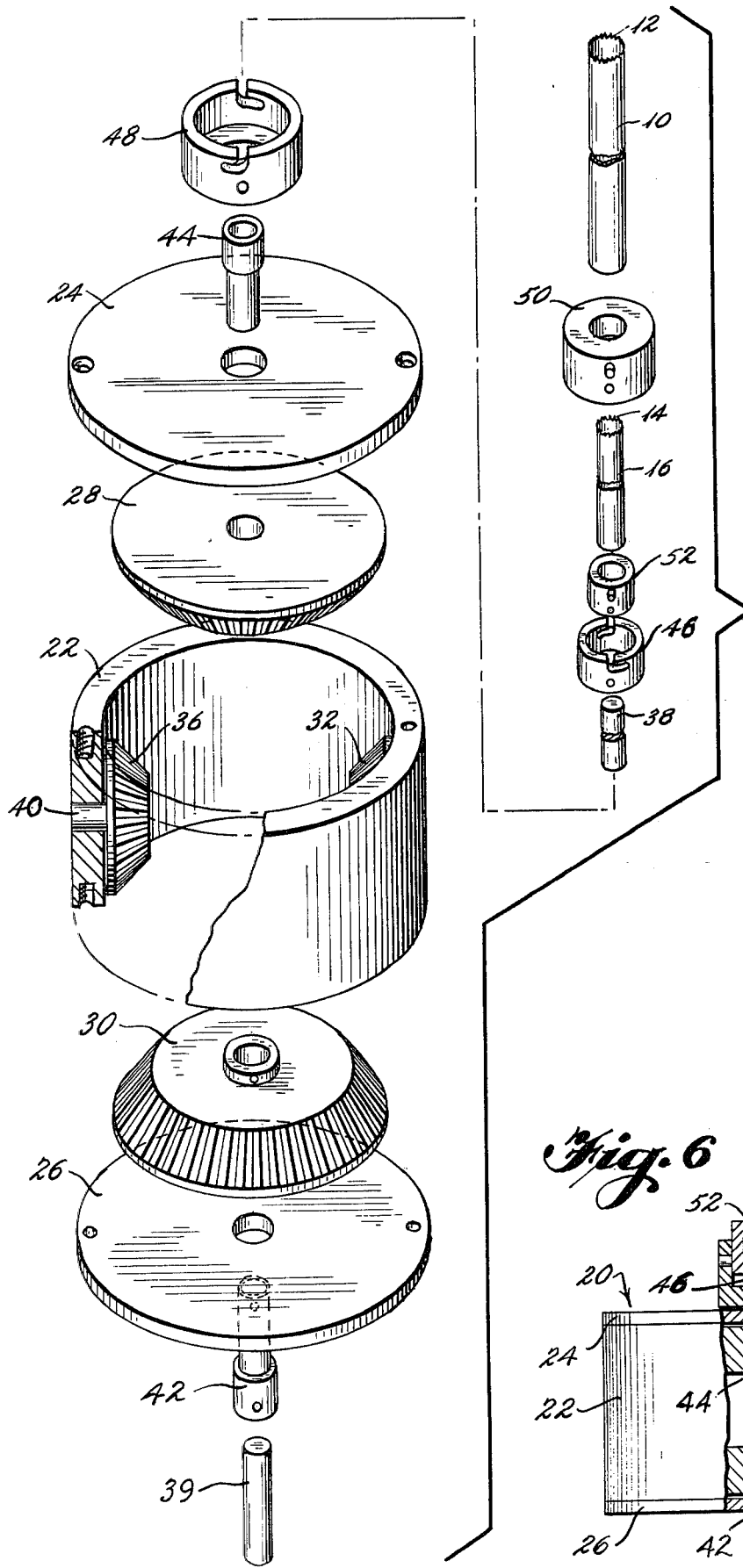
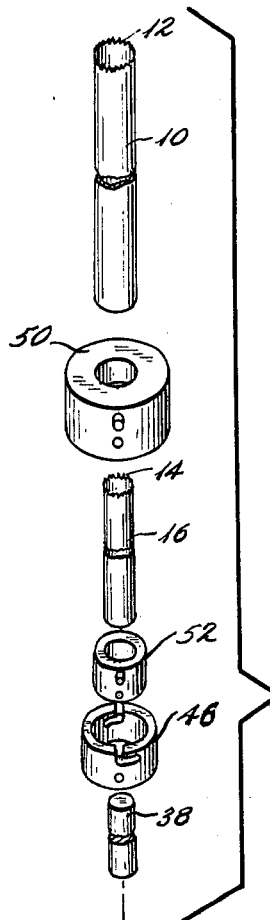
Fig. 5
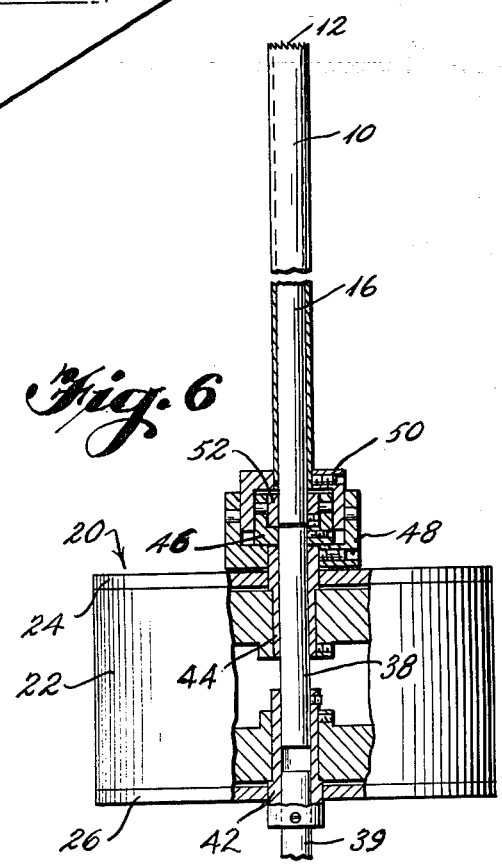
Fig. 6

COUNTER ROTATING BIOPSY NEEDLE

BACKGROUND OF THE INVENTION

1. Field of the Invention

This invention relates to biopsy needles, and more specifically to concentric biopsy needles adapted for counter-rotating movement for cutting through soft tissue and sawing through bone to obtain the desired sample.

2. Prior Art

A variety of needles is available to obtain samples of soft tissue. One standard class includes a closed tip needle with a side slot or opening near the tip. Soft tissue is sucked into the slot by means of applied vacuum. A cutter is used to separate the material which has been sucked in from the surrounding tissue. This type of needle is used predominantly for biopsy of the synovial lining of joints, but may also be used for liver, spleen, kidney and other soft tissues or organs.

A needle disclosed in Perez et al, U.S. Pat. No. 2,541,542 utilizes a loop of thread, extending from a cannula which has been advanced to a desired position with the aid of a style, to cut a section of tissue. The thread is tensioned to cut the tissue and to hold the same during withdrawal of the needle.

Baylis et al provide an elongated inner needle for initial penetration of body tissue in U.S. Pat. No. 4,177,797. An outer hollow cylindrical cutting tube is slidably received over the needle member until it also penetrates the body tissue. Both the tube and needle are then simultaneously withdrawn with the sample collected interiorly of the tube.

Banko U.S. Pat. No. 3,732,858 teaches the possible use of an electric motor for revolution of inner and outer jaws relative to one another, from an open to a closed position, as disclosed at columns 7 and 11 therein, for example. Relative rotation of a drill-like structure in conjunction with suction means is used to contain and progressively remove portions of a cutting.

Hallac U.S. Pat. No. 3,605,721 discloses a fixedly connected (soldered) coaxial inner and outer combination of needles 16 and 12 in conjunction with trochar 20. Needle 16 is telescopically received within needle 12. Both needles are provided with generally V-shaped coincident prongs. The connection between the needles collapses upon relative motion therebetween, thus capturing the biopsy specimen.

Jamshidi U.S. Pat. No. 3,628,524 provides a double sawtooth cutting edge in a biopsy needle for cutting soft tissue, such as liver, kidney, spleen, skin, muscle, etc., while a rasplike exterior surface is used for bone specimens. The needle is described as providing specimens without damage through crushing.

A variety of sawtooth ended cannulas, with or without outer sleeves or inner trochars, have been devised to obtain bone samples and samples of the intervertebral disc. Ackermann U.S. Pat. No. 2,919,692, for example, manually rotates a trephine 9, having six very fine sharp teeth undercut on their leading edges, for sawing purposes in a vertebral biopsy, within a guide 3.

Hofsess U.S. Pat. No. 3,893,445 is a further disclosure of a trephine cannula with multiple sawtooth design.

Another soft tissue device, disclosed in Steward U.S. Pat. No. 3,175,554, includes a first needle which is introduced to the area of interest along with a fitted stylet. A hollow bifurcated inner needle is inserted through and beyond the first needle. Camming action causes the needle to spread and to capture a sample of soft tissue. Withdrawl of the bifurcated needle leads, by camming action, to contraction of the portions thereof to contact each other, thus severing and trapping the biopsy within the split needle.

Hevesy U.S. Pat. No. 3,949,747 teaches the use of interchangeable ends in a biopsy set.

Other U.S. patents known to relate to biopsy devices include Cromer et al U.S. Pat. No. 2,710,000; Eskridge et al U.S. Pat. No. 3,683,891; Jamshidi U.S. Pat. No. 3,800,783 and Lacey U.S. Pat. No. 3,913,566.

A United Kingdom patent application (GB No. 2,022,421) discloses the use of a punch assembly 3, axially extensible from a shaft 1 having a prong-shaped cutting edge 1a. The apparatus requires successive punching operations to extract a sample.

However, none of the suction-type devices can penetrate cortical bone dependably. None preserve the natural architecture or orientation of tissue or cell types within the specimen. Since an accurate diagnosis frequently depends on an appreciation for the geometric relationships of one or more tissue types to others, it may occur that, even in soft tissue, no diagnosis can be made.

The forked needle type of needle also cannot biopsy bone and tends to mutilate the architecture of the specimen.

All of the sawtooth tip bone biopsy needles macerate and destroy much of the organization and architecture of the soft tissue and often the tumor system being examined. In essence, these devices saw a core of bone, cortical and/or trabecular, but work poorly with soft tissues. All presently used sawtooth ended trephines and needles grossly macerate the soft tissue or tumor tissue, thus destroying the organization and architecture, the relations of one tissue type to another, and make diagnosis of many tumors or pathologic conditions difficult or impossible.

The thin, small soft tissue needles, whether suction or mechanical in action, are not strong enough or appropriate for bone biopsy. Any attempt to use such needles in this way may subject them to a great risk of breakage within the patient. All such soft tissue needles compress, harm, and macerate the tissue to some extent, such that diagnosis dependent upon tissue architecture may be impossible to be made reliably.

Simple needles, while useful in the diagnosis of infection, rarely obtain enough tissue for tumor diagnosis. Such simple needles are typically useful only for aspiration of cavities where a diagnosis can be made from a smear of diseased cells.

SUMMARY AND OBJECTS OF THE INVENTION

It is accordingly a primary object of the invention to provide a biopsy needle capable of withdrawing a sample of tissue without maceration, thus overcoming many of the disadvantages of the prior art.

It is still another object of the invention to provide a single biopsy needle which may be used for obtaining both bone and soft tissue samples.

Yet another object of the invention is the provision of an easily cared for and easily sterilized biopsy instrument.

A further object of the invention is the provision of an easily inserted biopsy needle, using electric or air powered motors for rotation and freeing the operating surgeon to concentrate on guidance, rather than penetration of the needle.

Still a further object of the invention is the provision of a needle capable of withdrawing longer specimens than may typically be obtained by the prior art.

It is another object of the invention to provide a biopsy device which may be used under image intensifier control to biopsy lumbar vertebral bodies and/or intervertebral discs.

Yet another object of the invention is the provision of a gear arrangement for providing counter rotating biopsy needles.

Still a further object of the invention is the provision of interchangeable biopsy needles for use in obtaining biopsy samples.

In accordance with the foregoing objects, the present invention provides a counter-rotating set of concentric tubes, having sawteeth at the distal ends thereof for sawing through bone or cutting through tissue, and a means for rotating the tubes, the rotating means being connected to the proximate ends of the tubes. A means for severing and extracting the core of biopsy material is provided in conjunction with the counter-rotating sawteeth.

The provided sawteeth face in opposite directions on the two tubes to provide the desired sawing and cutting operation for bone and soft tissues, respectively. The rotating means typically comprises a gear system which includes a bevelled gear driving each tube, and an idler gear engaging both the bevelled driving gears to provide opposite rotation for the two gears. One of the gears is driven by a rotor shaft which may be driven by an electric or an air motor.

In accordance with still further objects of the invention, two elongated concentric tubes which are interchangeable with other similar tubes are provided with clockwise and counter-clockwise facing teeth on their respective distal ends. A gear system includes matching bevelled gears connected to the two tubes, along with at least one bevelled idler gear engaging the matching bevelled gears. One of the gears is driven by a rotor shaft thereby rotating one of the tubes in a clockwise direction and the other of the tubes in a counter-clockwise direction.

The device may be provided with interchangeable tubes which are coupled at their proximate ends to the gear system by a coupling means. The coupling means includes inner and outer rotor shaft adaptors driven by the two bevelled gears, and inner and outer rotor heads connected to the respective rotor shaft adaptors. The tubes, which are concentrically and telescopically disposed, include coupling heads for coupling the inner tube with the inner rotor head and for coupling the outer tube with the outer rotor head.

The foregoing and other objects, features and advantages of the present invention will become more readily apparent to those skilled in the art from the following specification and claims, when considered in conjunction with the accompanying drawings.

BRIEF DESCRIPTION OF THE DRAWINGS

FIG. 1 shows an outer tube for use with the present invention;

FIG. 2 shows an inner tube for use with the present invention;

FIG. 3 illustrates, partially in cross section, a counter rotating biopsy needle assembly according to the present invention;

FIG. 4 shows the tubes of FIGS. 1 and 2 in telescoping engagement;

FIG. 5 shows an exploded view and FIG. 6 shows an assembled view, partially in cross section, of a modified arrangement of the counter rotating biopsy needle, including the various components of the gear assembly, changeable coupling, tubes and rotor shaft used in the present invention.

DETAILED DESCRIPTION OF A PREFERRED EMBODIMENT

In accordance with the above described objects of the invention, a counter-rotating universal needle provides a pathologist with a core of tissue containing normal tissue, the surface of a lesion, the active outer layer and the inner core of a tumor, all in one cylinder without separation or maceration. The needle structure permits cutting samples of skin, muscle, fascia, trabecular bone or cortical bone. Specially designed cutter tubes make the instrument appropriate for disk lesions, very soft lesions, or breast biopsy. Because of its simple structure, the instrument may be sterilized using a standard autoclave.

The inventive structure includes two thin walled, telescoping concentric tubes which fit accurately together. The tubes are shown in FIGS. 1 and 2, while FIG. 4 illustrates the inner and outer tubes telescoped together for use.

As seen in FIG. 1, an outer tube 10 is provided with sawteeth 12 facing in a counter-clockwise rotational direction, formed on its distal tip. Similar sawteeth 14 facing in the opposite rotational direction (clockwise) are formed on the distal end of the inner tube 16. The directions are established when viewed from the proximal to the distal end. The two tubes are concentrically disposed in a telescoping fashion as shown in FIG. 4. It is appreciated, however, that the sawteeth 12 on the tube 10 could face in a clockwise rotational direction. Similar sawteeth 14 on the distal end of the tube 16 would then face in a counter-clockwise rotational direction and the tubes would be made to counter-rotate appropriately to assure the described cutting and sawing action.

Mechanical interconnection of the tubes is provided by a gear system, broadly shown in FIG. 3 at reference numeral 20.

The connecting gear system is contained in a housing 22 which may be circular. A pair of covers 24 and 26 enclose the housing and the gears situated therein.

A pair of large matching bevel gears 28, 30 are enclosed within housing 22 by covers 24 and 26. Gear 28 includes a central opening with a diameter sufficiently large to engage the outer diameter of outer tube 10, while gear 30 includes a smaller opening, sufficient to engage the outer diameter of inner tube 16. Also enclosed within housing 22 is at least a single idler gear 32, also bevelled for engaging gears 28 and 30.

Idler gear 32 is preferably mounted on a bearing shaft 34 formed within the housing, although other supporting means may be used. At the diametrically opposed location in housing 22, a second gear may be located for separating and supporting gears 28 and 30. It is appreciated, however, that rather than a gear 36, other support members may be used. For example, a bearing surface may be provided within the housing to separate and rigidly maintain the positioning of the large bevelled gears.

Tubes 10 and 16 are mounted in a gear case by inserting the tubes within one another as shown in FIG. 4, with an extension of inner tube 16 passing through the outer tube 10, through gear 28, and into driving contact with gear 30. Tube 10, however, extends only as far as gear 28 in order not to interfere with the gears in housing 22. Both tubes 10 and 16 may be retained in the respective gears 28 and 30 by conventional means, such as set screws, keyed shafts or the like.

As shown in FIG. 3, inner tube 16 may extend substantially beyond bevel gear 30 and may receive a driving force directly for imparting rotation to bevel gear 30 through support bearing 41. In turn, idler gear 32 is rotated causing bevel gear 28 to rotate outer tube 10 in the opposite direction through support bearing 43. Alternatively, inner tube 16 can terminate below outer tube 10 in the space between bevel gears 28 and 30. In this case, a separate drive shaft (not shown) can be connected by suitable coupling means to the exposed end of tube 16.

In the embodiment of FIGS. 5 and 6, where the same reference numerals have been used for the same components, a modified form of drive system is illustrated for use in conjunction with the interchangeable cutting tubes. A separate drive or rotor shaft 39 is attached in driving relationship to lower bevel gear 30 and also in driving relationship with driven shaft 38 via adaptor 42. Rotation of shaft 38 is transmitted to tube 16 in one direction and tube 10 in the opposite direction by virtue of the interchangeable coupling system to be described below. In general, however, application of rotary driving force by rotor shaft 39 to bevel gear 30 causes transmission of the resulting rotary motion, in a reverse direction, to gear 28 by way of idler gears 32 and 36, as with the embodiment of FIG. 3.

The rotary driving force provided to the rotor shaft may be manually applied or may be applied by an air or electrically powered motor. While such rotation is intended to be applied to the rotor shaft 39 or extended inner tube 16 with respect to a stationary housing, it is clear that slippage of the housing will merely result in reduction of the relative speed between the tubes, and may in fact be used to control such relative speeds.

As an alternative source of rotary power, it is possible that gear mount 40 for idler 36 may, in fact be a driven rotor. In that event, the gear system will continue to provide the counter-rotating motion to the two tubes 10 and 16. Such a driving relationship may be achieved by penetrating housing 22 with a drive shaft for contacting and driving mount 40 and, in turn, idler 36.

Of course, the use of additional idler bevel gears may be desired, such additional idler gears being preferably equally spaced about the periphery of housing 22.

Not shown in the figures, but contemplated for use in conjunction with the foregoing structure is a thin-walled cannula or tube and matching blunt or sharp trochar or obdurator. With the trochar positioned in the cannula, said cannula can be inserted safely through normal tissue to the position where the planned biopsy should start. The trochar or obdurator is removed and the biopsy needle inserted through the positioned tube or cannula.

Thus, having reached the desired location, the tubes may be made to rotate in opposite directions, thereby causing sawteeth 12 and 14 to act as scissors when passing through soft tissue, muscle, fat, skin, tendons, kidney, liver, as well as tumor, while also cleanly sawing through both cortical and trabecular bone.

Also contemplated for use, but not shown in the figures, is an inner plunger or rod of length equal to or slightly greater than the described tubes 10 and 16. After removal of the biopsy device, the plunger rod can be inserted from the driven end into tube 16 toward the cutting tips. This plunger is used to propulse the biopsy specimen material out from the inner tube.

A further feature of the device is the availability of an option for interchangeable tubes or cutting heads. As shown in FIGS. 5 and 6, a coupling system may be interposed between the tubes and the gear system, to enable quick decoupling and recoupling of varying tubes and cutters to the gears. Specifically, a first rotor shaft adaptor 42 may be inserted in bevel gear 30, while a second rotor shaft adaptor 44 is inserted in bevel gear 28. Adaptor 44 is attached to an opening in an outer rotor head 48 and transmits rotary motion thereto. Adaptor 42 is connected to shaft 38 which is connected to an inner rotor head 46 which is rotated by the action of the gear system as previously described. The outer tube 10 and inner tube 16 are provided, respectively, with outer needle head 50 and inner needle head 52 for coupling to rotor heads 48 and 46, respectively.

Therefore, in operation, rotation of shaft 39 is transmitted in the same direction to adaptor 42 and rotor shaft 38 and causes rotation of bevel gear 30. The rotation of shaft 38 is transmitted to rotor head 46, needle head 52 and inner tube 10, all in the same rotary direction as shaft 39. At the same time, rotation of bevel gear 30 cause the opposite rotation of upper bevel gear 28 through provision of idler gear 32. This reverse rotation is transmitted to second rotor shaft adaptor 44, rotor head 48, outer needle head 50 and outer tube 10. Opposite rotation of the inner and outer cutting teeth 14 and 12 is, thus, obtained.

Accordingly, it is seen that different length tubes may be easily coupled to the present biopsy needle, as well as different diameter cutters to be substituted. Alternatively, the tubes may be removed for sharpening of the cutters or for replacement by new, sharpened cutters.

Typical diameters for the outer tube may be approximately 5-6 millimeters, while the inner tube will be selected for a close fit with the inner dimensions of the outer tube. However, various sizes of biopsy needles can be adapted to the same gear housing. For example, 3/16" outer diameter needles for disc space biopsies; ¼" outer diameter needles may be a standard needle size, and ⅜" outer diameter needles may be used for soft tissue biopsy.

In view of the disclosed structure, it is further apparent that cores of substantially longer specimens may be obtained than by other present means, the length depending upon the length of the tubes used for the specific procedure.

Further, the rotary nature of the device readily lends itself to the use of external motor driving power, so that the surgeon can concentrate on positioning an accurate direction of the cutting edge instead of on twisting a T-handle or manually turning a crank. The present needle can often be used with biplanar image intensification to provide an ample specimen and at the same time to document the exact location from which the tissue was obtained. Such image intensifier control may be used, for example, to biopsy lumbar vertebral bodies and/or intervertebral discs. Such a safe and certain biopsy procedure could thus eliminate the need for "open" biopsy in many cases, and should, therefore, save operating room time for more extensive surgical procedures.

Having penetrated and obtained the sample, the present device may further include any of a variety of grabbers, screw devices or forceps, as known in the art, to extract the core of biopsy material.

It is also appreciated that liquid gases or other sources of cold may be used to preserve the tissue core architecture and organization during extrusion from the present device.

The preceding specification describes, by way of illustration and not of limitation, a preferred embodiment of the invention. Equivalent variations of the described embodiment will occur to those skilled in the art. For example, any of a number of differential, spider, or spur gear arrangements could be designed to accomplish the desired counter-rotation of the tubes, such alternative arrangements providing ease of manufacture, greater dependability or a more pleasing appearance.

Other variations may include a pistol grip design for greater surgical control; a small spur idler gear could be powered to offset the motor and provide a side grip; replaceable or disposable cutter tubes may be developed; any tooth size or configuration could be manufactured; any length of concentric tubes could be provided, and any appropriate outside diameter of the concentric tubes might be preferred.

Such modifications, variations and equivalents are within the scope of the invention as recited with greater particularity in the following claims, when interpreted to obtain the benefits of all equivalents to which the invention is fairly entitled.

I claim:

1. A biopsy needle for cutting and removal of a core sample of bone or tissue comprising:
   (a) first and second tubes comprised of elongated concentric tubular components each having distal and proximate ends;
   (b) rotating means connected to said components at the proximate ends thereof for providing counter-rotating motion to said first and second tubes; and
   (c) sawteeth provided at the distal ends of said first and second tubes for sawing through bone or cutting through tissue.

2. A biopsy needle as recited in claim 1 wherein said sawteeth include a first set of teeth facing in a clockwise rotational direction and a second set of teeth facing in a counter-clockwise rotational direction, said first set being formed on the distal end of one of said first and second tubes, said second set being formed on the distal end of the other of said first and second tubes.

3. A biopsy needle as recited in claim 2 wherein said one of said first and second tubes is the inner tube.

4. A biopsy needle as recited in claim 1 wherein said rotating means comprises a gear system for counter rotation.

5. A biopsy needle as recited in claim 4 wherein said gear system includes a housing, said housing having a first gear connected to said first tube and a second gear connected to said second tube, said first tube being disposed internally of said second tube.

6. A biopsy needle as recited in claim 5 wherein said first and second gears are matching bevelled gears, said gear system further including at least one bevelled idler gear engaging said first and second bevelled gears.

7. A biopsy needle as recited in claim 6 wherein said at least one idler gear is mounted on a bearing shaft associated with a surface of said housing.

8. A biopsy needle as recited in claim 7 further comprising a driving pinion for said first and second matching bevelled gears, said driving pinion being driven by an external drive shaft driven, in turn, by a driving motor.

9. A biopsy needle as recited in claim 7 comprising two idler gears, at least one of said idler gears mounted on a bearing shaft associated with said housing.

10. A biopsy needle as recited in claim 7 comprising three idler gears, at least one of said idler gears mounted on a bearing shaft associated with said housing.

11. A biopsy needle as recited in claim 7 further comprising a rotor shaft for driving one of said first and second gears, whereby the tube connected to said one driven gear is driven in one rotational direction and the tube driven by the other of said first and second gears is driven in an opposite rotational direction.

12. A biopsy needle as recited in claim 7 further comprising a rotary shaft for driving one of said idler gears whereby the tube connected to said first gear is driven in one rotational direction and the tube connected to said second gear is driven in the opposite rotational direction.

13. A biopsy needle as recited in claim 11 wherein said one driven gear is said first gear connected to said first tube disposed internally of said second tube.

14. A biopsy needle as recited in claim 11 further comprising a motor means for driving said rotor shaft.

15. A biopsy needle as recited in claim 14 wherein said motor means comprises an electrically driven motor unit.

16. A biopsy needle as recited in claim 14 wherein said motor means comprises an air powered motor unit.

17. A biopsy needle as recited in claim 7 further comprising an outer cannula and matched trochar for enabling insertion of the apparatus to a position where a desired biopsied specimen is located.

18. A biopsy needle for cutting and removal of a core sample of bone or tissue comprising:
   (a) first and second changeable elongated concentric tubes eaching having distal and proximate ends;
   (b) a first set of teeth facing in a clockwise rotational direction and a second set of teeth facing in a counter clockwise rotational direction, said first set being formed on the distal end of one of said first and second tubes, said second set being formed on the distal end of the other of said first and second tubes;
   (c) a gear system for providing counter-rotating motions to said first and second tubes, including a housing having:
      (i) a first bevelled gear connected to said first tube,
      (ii) a second matching bevelled gear connected to said second tube, and
      (iii) at least one bevelled idler gear engaging said first and second bevelled gears;
   (d) wherein a means for driving one of said first and second bevelled gears rotates said one of said first and second tubes in a clockwise direction and said other of said first and second tubes in a counter-clockwise direction.

19. A gear system as recited in claim 18 wherein said means for driving is a rotor shaft connected to one of said first and second bevelled gears.

20. A gear system as recited in claim 18 wherein said means for driving is a rotor shaft connected to one of said at least one bevelled idler gear.

21. A biopsy needle as recited in claim 18 further comprising means for changeably coupling proximate ends of said tubes to said gear system.

22. A biopsy needle as recited in claim 21 wherein said means for changeably coupling comprises:
 (a) first rotor shaft adaptor driven by said first bevelled gear;
 (b) second rotor shaft adaptor driven by said second bevelled gear;
 (c) outer rotor head means connected to said second rotor shaft adaptor, and
 (d) inner rotor head means connected to said first rotor shaft adaptor.

23. A biopsy needle as recited in claim 22 wherein said first tube is an inner tube located concentrically and telescopically within said second tube, said first tube including an inner needle head for coupling with said inner rotor head means, said second tube including an outer needle head for coupling with said outer rotor head means, whereby said rotor and needle heads may be decoupled from each other for substituting a different set of tubes and heads for coupling to said gear system.

* * * * *